(12) United States Patent

Barkóczy et al.

(10) Patent No.: US 7,183,283 B2
(45) Date of Patent: Feb. 27, 2007

(54) PIPERIDINYL-ALKYLAMINO-PYRIDAZINONE DERIVATIVES, A PROCESS FOR THE PREPARATION THEREOF AND PHARMACEUTICAL COMPOSITIONS CONTAINING SAID COMPOUNDS

(75) Inventors: József Barkóczy, Budapest (HU); István Gacsályi, Budapest (HU); László Gábor Hársing, Budapest (HU); Péter Kótay Nagy, Vác (HU); György Lévay, Budakeszi (HU); Éva Schmidt, Budapest (HU); Gyula Simig, Budapest (HU)

(73) Assignee: Egis Gyogyszergyar RT., Budapest (HU)

( * ) Notice: Subject to any disclaimer, the term of this patent is extended or adjusted under 35 U.S.C. 154(b) by 0 days.

(21) Appl. No.: 10/508,676

(22) PCT Filed: Dec. 28, 2002

(86) PCT No.: PCT/HU02/00171

§ 371 (c)(1),
(2), (4) Date: May 25, 2005

(87) PCT Pub. No.: WO03/091244

PCT Pub. Date: Nov. 6, 2003

(65) Prior Publication Data

US 2005/0215560 A1   Sep. 29, 2005

(30) Foreign Application Priority Data

Apr. 26, 2002   (HU) .................................... 0201374

(51) Int. Cl.
*C07D 401/12*   (2006.01)
*C07D 401/14*   (2006.01)
*A61K 31/501*   (2006.01)
*A61P 25/22*   (2006.01)

(52) U.S. Cl. ................. 514/252.03; 544/238
(58) Field of Classification Search ................ 544/238; 514/252.03
See application file for complete search history.

(56) References Cited

FOREIGN PATENT DOCUMENTS

WO   WO-03/010166 A   2/2003

OTHER PUBLICATIONS

Borsini et al. (2002) Do animals models of anxiety predict anxiolytic-like effects of antidepressants? Psychopharmacology 163:121-141.*
Weems et al. Clinical Child and Family Psychology Review, vol. 8, No. 2, Jun. 2005 (pp. 107-134).*
Abstract from Rynn et al. J. Clin Psychiatry, 2002; 63 Suppl 14: 9-16 (one page).*
Corsano, S. et al., "New 3(2H)-Pyridazinone Derivatives: Synthesis and Affinity Towards Alpha(1)AR Subtypes and 5HT(1A) Receptors", European Journal of Medicinal Chemistry Editions Scientifique Elsevier, Paris, France. vol. 32, No. 4, 1997, pp. 339-342.

* cited by examiner

*Primary Examiner*—Kahsay Habte
(74) *Attorney, Agent, or Firm*—Birch, Stewart, Kolach & Birch, LLP

(57) ABSTRACT

The invention relates to new piperidinyl-alkylamino-pyridazinone derivatives of the general Formula (I) (wherein R is hydrogen or $C_{1-4}$-alkyl; one of X and Y stands for hydrogen and the other represents a group of the general Formula (II) Hal stands for halogen; and n is 1 or 2) and pharmaceutically acceptable acid addition salts thereof a process for the preparation thereof and pharmaceutical compositions comprising said compounds. The compounds of the general Formula I exhibit anxiolytic effect and are useful in the treatment of anxiety

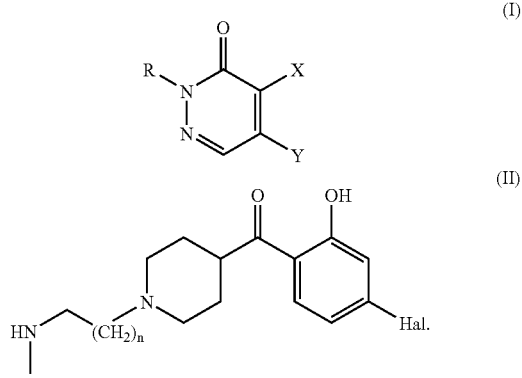

10 Claims, No Drawings

PIPERIDINYL-ALKYLAMINO-PYRIDAZINONE DERIVATIVES, A PROCESS FOR THE PREPARATION THEREOF AND PHARMACEUTICAL COMPOSITIONS CONTAINING SAID COMPOUNDS

FIELD OF THE INVENTION

The invention relates to new piperidinyl-alkylamino-pyridazinone derivatives, a process for the preparation thereof and pharmaceutical compositions containing said compounds.

The new compounds of the invention exhibit anxiolytic effect and are useful in the treatment of human anxiety disorders.

TECHNICAL BACKGROUND OF THE INVENTION

Research directed to the development of active ingredients suitable for the treatment of anxiety is one of the most important fields of pharmaceutical research. The reason of this is that the occurrence of anxiety is extremely high in normal populations. According to statistics the ratio of anxiety is generally 4–10% per year but pursuant to certain estimations it can even reach 20% of the population [Ad Sitsen, J. M., Current Trends in Anxiolytic Research, Scrip, (1992) March].

Anxiety is not a separate disease entity but rather a generic term which encompasses groups of psychiatric clinical patterns (generalized anxiety disorder, panic disease, compulsive disorder, post-traumatic stress disorder etc.). For the time being the most accepted diagnostic system for the classification of anxiolytic clinical pictures is the DSM-IV system published by the American Psychiatric Society.

For the treatment of anxiety disorders most widespreadly compounds having a benzodiazepine structure and compounds having no benzodiazepine structure but binding to the GABA-benzodiazepine-Cl$^-$ ion complex (e.g. diazepam, alprazolam, meprobamat, clonazepam) are used. Benzodiazepine type anxiolytics are accompanied, however, by several undesired side-effects (e.g. sedation, muscle relaxant effect, dependency etc.) Said side-effects influence the quality of life of the patients in an adverse manner. Besides benzodiazepine type medicines only a few other active ingredients are commercially available (e.g. buspiron) which enable alternative treatment. In case of buspiron therapeutical effect can be achieved only after a treatment lasting for at least 12–14 days.

Neuroleptic 3-(1-substituted-4-piperidinyl)-1,2-benzisoxazole derivatives are described in J. Med. Chem., 28(6), 761–769 (1985). Antiarrhythmic 3(2H)-pyridazinone derivatives are known from U.S. Pat. No. 5,395,934.

SUMMARY OF THE INVENTION

The object of the present invention is to develop anxiolytic active ingredients which are free of the above undesired side-effects and are effective already after a short treatment period.

The above object is achieved by the new piperidinyl-alkylamino-pyridazinone derivatives of the general Formula

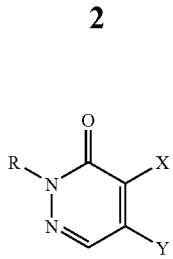

of the present invention.

The invention relates to new piperidinyl-alkylamino-pyridazinone derivatives of the general Formula I (wherein R is hydrogen or $C_{1-4}$-alkyl;

one of X and Y stands for hydrogen and the other represents a group of the general Formula

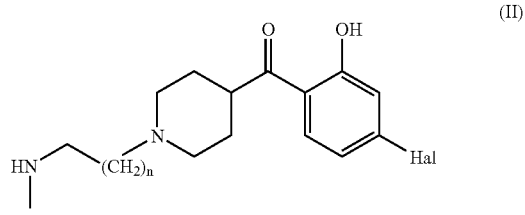

Hal stands for halogen; and n is 1 or 2)

and pharmaceutically acceptable acid addition salts thereof.

DETAILED DESCRIPTION OF THE INVENTION

The definition of the terms used in the present patent specification are as follows:

The term "$C_{1-4}$-alkyl" relates to straight or branched chain saturated hydrocarbon groups having 1–4 carbon atoms (e.g. methyl, ethyl, isopropyl, n-propyl, n-butyl, sec. butyl, isobutyl or tert. butyl, preferably methyl).

The term "halogen" encompasses the fluorine, chlorine, bromine and iodine atoms and is preferably fluorine.

The "pharmaceutically acceptable acid addition salts of the compounds of the general Formula I" may be formed with inorganic acids (e.g. hydrochloric acid, hydrogen bromide, sulfuric acid, phosporic acid etc.) or organic acids (e.g. formic acid, acetic acid, maleic acid, fumaric acid, lactic acid, tartaric acid, succinic acid, citric acid, benzenesulfonic acid, p-toluenesulfonic acid, methanesulfonic acid etc.). The pharmaceutically acceptable acid addition salts must be non-toxic.

According to a preferred embodiment of the present invention there are provided piperidinyl-alkylamino-pyridazinone derivatives of the general Formula I wherein Y is a group of the general Formula II, X stands for hydrogen and R, Hal and n are as stated above.

According to a particularly preferable embodiment of the present invention there are provided piperidinyl-alkylamino-pyridazinone derivatives of the general Formula I wherein Y is a group of the general Formula II, X is hydrogen, R is hydrogen or methyl, Hal is fluorine and n is 1 or 2.

Particularly advantageous representatives of the compounds of the present invention are the following derivatives:

5-{2-[4-[1-(4-fluoro-2-hydroxy-phenyl)-methanoyl]-piperidine-1-yl]-ethylamino}-2-methyl-2H-pyridazine-3-one, 5-{2-[4-[1-(4-fluoro-2-hydroxy-phenyl)-methanoyl]-piperidine-1-yl]-ethylamino}-2H-pyridazine-3-one, 5-{2-[4-[1-(4-fluoro-2-hydroxy-phenyl)-methanoyl]-piperidine-1-yl]-propylamino}-2-methyl-2H-pyridazine-3-one and pharmaceutically acceptable acid addition salts thereof.

According to a further aspect of the present invention there is provided a process for the preparation of piperidinyl-alkylamino-pyridazinone derivatives of the general Formula I and pharmaceutically acceptable acid addition salts thereof.

The piperidinyl-alkylamino-pyridazinone derivatives of the general Formula I and pharmaceutically acceptable acid addition salts thereof can be prepared by a) for the preparation of compounds of the general Formula I, wherein Y stands for a group of the general Formula II and X, R, n and Hal are as stated above, subjecting a benzisoxazolyl-piperidinyl-alkylamino-pyridazinone derivative of the general Formula I (wherein Y stands for a group of the general Formula

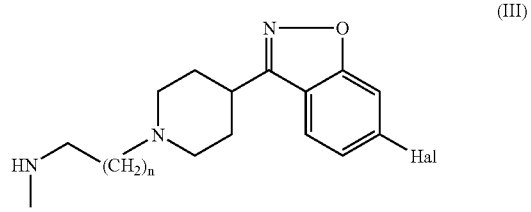

(III)

X stands for hydrogen or chlorine and R, Hal and n are as stated above to catalytic hydrogenation; or b) for the preparation of compounds of the general Formula I, wherein X stands for a group of the general Formula II and Y, R, Hal and n are as stated above, subjecting a benzisoxazolyl-piperidinyl-alkylamino-pyridazinone derivative of the general Formula I (wherein X is a group of the general Formula III, Y stands for hydrogen or chlorine and R, Hal and n are as stated above to catalytic hydrogenation;

and if desired converting a piperidinyl-alkylamino-pyridazinone derivative of the general Formula I thus obtained into a pharmaceutically acceptable acid addition salt thereof or setting free the base from its acid addition salt.

According to processes a) and b) starting materials corresponding to the invention compounds of the general Formula I are used in which one of the symbols X and Y stands for a group of the general Formula III and the other is hydrogen or chlorine, and R, Hal and n are as stated above. The starting material is subjected to catalytic hydrogenation. The reaction is carried out by methods known per se [see e.g. March, J.: Advanced Organic Chemistry, Reactions, mechanism and structure, 4$^{th}$ edition, John Wiley & Sons, New York, (1992)]. Catalysts generally used in such reactions can be applied e.g. palladium, Raney-nickel etc. It is preferred to use palladium, particularly on a charcoal carrier. As hydrogen source preferably gaseous hydrogen, hydrazine, hydrazine hydrate, formic acid, trialkyl ammonium formiate or alkyl formiates can be used.

Catalytic hydrogenation is carried out in an inert solvent. As reaction medium protic or aprotic solvents or mixtures thereof can be used. As protic solvent e.g. alkanols, preferably methanol, ethanol or mixtures thereof and as aprotic solvent e.g. dioxane, dichloro methane etc. can be used.

The reaction can be performed in the presence or absence of an acid binding agent. For this purpose organic and inorganic bases (e.g. hydrazine, triethyl amine, diisopropyl ethyl amine, sodium hydroxide, sodium hydrogen carbonate etc.) can be used.

Catalytic hydrogenation can be carried out at a temperature between 0° C. and 150° C., preferably at 20–100° C.

Benzisoxazolyl-piperidinyl-alkylamino-pyridazinone starting materials corresponding to the general Formula I, wherein X stands for hydrogen or chlorine and Y stands for a group of the general Formula III, can be prepared by reacting the corresponding alkylamino-pyridazinone of the general Formula

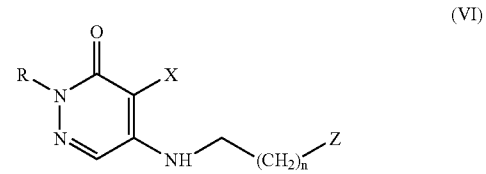

(VI)

(wherein X is hydrogen or chlorine, R and n are as stated at the general Formula I and Z is a leaving group) with a 6-halogeno-3-piperidine-4-yl-1,2-benzisoxazole of the general Formula

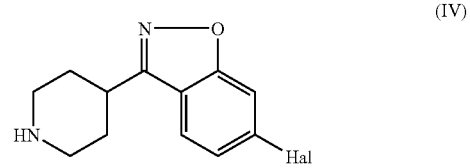

(IV)

(wherein Hal is halogen). Similarly benzisoxazolyl-piperidinyl-alkylamino-pyridazinone starting materials corresponding to the general Formula I, wherein Y stands for hydrogen or chlorine and X stands for a group of the general Formula III, can be prepared by reacting the corresponding alkylamino-pyridazinone of the general Formula

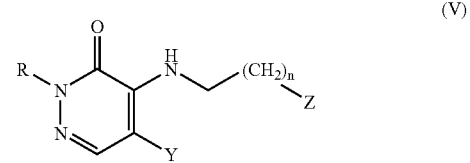

(V)

(wherein Y stands for hydrogen or chlorine, R and n are as stated at the general Formula I and Z is a leaving group) with a 6-halogeno-3-piperidine-4-yl-1,2-benzisoxazole of the general Formula IV (wherein Hal is halogen).

The alkylamino-pyridazinone derivatives of the general Formulae V and VI used as starting material can be prepared by the process disclosed in PCT/HU98/00054.

The 6-fluoro-3-piperidine-4-yl-1,2-benzisoxazole is described in J. Med. Chem., 28(6), 761–769 (1985).

The pharmacological effects of piperidinyl-alkylamino-pyridazinone derivatives of the general Formula I have been established in the following tests.

Anxiolytic Effect

Elevated Plus-maze

Tests have been performed as described by Pellow and co-workers [J. Neurosci. Methods, 14, 149 (1985)]. A wooden cross, 15 cm wide with 100 cm long arms was used for the experiments. The sides and ends of two opposite arms of the cross were equipped with 40 cm high walls, however, the arms were open to the 15×15 cm central area (closed arms). The two other opposite arms were not encircled by walls (open arms).

Male Sprague-Dawley rats weighing 200–220 g were used for the experiments. The animals were placed in the central area of the equipment 60 min after treatment and the following four parameters have been observed for the 5 min test time:

time spent in the open arms,
time spent in the closed arms,
number of entries into the open arms,
number of entries into the closed arms.

The effect was expressed as percent increase in either the time (measured in sec) spent in the open arms or number of entries into the open arms. MEDs (minimal effective dose) were determined for each compound regarding the time spent in the open arms. Results are summarized in Table I. Buspiron [8-[4-[4-(2-pyrimidinyl)-1-piperazinyl]-butyl]-8-azaspiro[4,5]decan-7,9-dion] was used as reference compound.

TABLE I

Elevated plus-maze in rats

| Compound (Example No) | MED (mg/kg po) |
|---|---|
| 1 | ≦0.03 |
| 2 | ≦0.3 |
| 3 | ≦0.3 |
| Buspiron | 3.0 |

Data in Table I show that the examined compounds according to the invention display anxiolytic effect one or two order of magnitude higher than that of buspiron used extensively in therapy.

Sedative Effect

Inhibition of Spontaneous Motor Activity

The effect on spontaneous motor activity was investigated according to Borsy and co-workers [Borsy, J. et al, Arch. Int. Pharmacodyn., 124, 180–190 (1960)] in a ten channel Dews instrument, with 1—1 animal in each channel. Animals were placed into the instrument 60 min after per os treatment with either vehicle or test compound, and interruptions of infrared beams were recorded for 30 min. From these data, 50 percent inhibitory doses ($ID_{50}$) have been determined by regression analysis. Data obtained are summarized in Table II. Diazepam [7-chloro-1,3-dihydro-1-methyl-5-phenyl-2H-1,4-benzodiazepine-2-one] was used as reference compound.

TABLE II

Inhibition of spontaneous motor activity in mice

| Compound (Example No) | $ID_{50}$ (mg/kg po) |
|---|---|
| 1 | >100 |
| 2 | >100 |
| 3 | >100 |
| Diazepam | 7.0 |

Data in Table II show that on the contrary to diazepam, the examined compounds according to the invention display no sedative effects even in very high dose (100 mg/kg).

Thus, the piperidinyl-alkylamino-pyridazinone derivatives of the general Formula I show significant anxiolytic activity without decreasing vigilance by displaying sedative side effects in the therapeutic dose range, therefore the compounds could be of use in the therapy of human anxiety disorders.

Thus the compounds of the general Formula I and pharmaceutically acceptable acid addition salts thereof can be used as pharmaceutical active ingredients.

According to a further aspect of the present invention there are provided pharmaceutical compositions comprising as active ingredient a piperidinyl-alkylamino-pyridazinone derivative of the general Formula I (wherein X, Y, R, Hal and n are as stated above or a pharmaceutically acceptable acid addition salt thereof in admixture with usual carrier(s).

The pharmaceutical compositions according to the present invention contain generally 0.1–95% by weight, preferably 1–50% by weight, particularly 5–30% by weight of the active ingredient, related to the total weight of the composition.

The pharmaceutical compositions according to the present invention can be administered orally, parenterally, rectally, transdermally or can be used topically. The composition can be solid or liquid.

The solid pharmaceutical compositions suitable for oral administration can be powders, capsules, tablets, film-coated tablets, microcapsules etc. Such compositions can contain binders (e.g. gelatine, sorbitol, polyvinylpyrrolidone etc.), fillers (e.g. lactose, glucose, starch, calcium phosphate etc.), tabletting auxiliary agents (e.g. magnesium stearate, talc, polyethylene glycol, silicium dioxide etc.), wetting agents (e.g. sodium lauryl sulfate etc.).

The liquid compositions suitable for oral administration can be solutions, suspensions or emulsions. Such compositions can contain e.g. suspending agents (e.g. gelatine, carboxymethyl cellulose), emulsifiers (e.g. sorbitane monooleate etc.), solvents (e.g. water, oils, glycerol, propyleneglycol, ethanol), preservatives (e.g. methyl-p-hydroxybenzoate, propyl-p-hydroxy-benzoate etc.).

Pharmaceutical compositions suitable for parenteral administration are generally sterile solutions of the active ingredient.

The above dosage forms mentioned for the sake of exemplification and also other dosage forms are known per se [see Remington's Pharmaceutical Sciences, 18$^{th}$ edition, Mack Publishing Co., Easton, USA (1990)].

The pharmaceutical compositions according to the present invention contain generally a dosage unit. The daily dosage for human adults can be generally 0.1–1000 mg/kg body weight of a compound of the general Formula I or a pharmaceutically acceptable acid addition salt thereof. Said daily dose can be administered in one or more portion(s). The actual daily dose depends on several factors and is determined by the physician.

According to a further aspect of the present invention there is provided a process for the preparation of pharmaceutical compositions which comprises admixing a compound of the general Formula I or a pharmaceutically acceptable acid addition salt thereof with suitable pharmaceutical carriers and/or auxiliary agents. The pharmaceutical compositions are prepared by known methods of pharmaceutical industry. Said methods are disclosed e.g. in the above mentioned Remington's Pharmaceutical Sciences reference.

As active ingredient preferably piperidinyl-alkylamino-pyridazinone derivatives of the general Formula I can be used in which Y stands for a group of the general Formula II;

X represents hydrogen; and

R, Hal and n are as stated above.

As active ingredient particularly preferably piperidinyl-alkylamino-pyridazinone derivatives of the general Formula I can be used in which Y stands for a group of the general Formula II;

X represents hydrogen;

R stands for methyl;

Hal stands for fluorine; and n is 1 or 2.

The pharmaceutical compositions according to the present invention can particularly preferably contain 5-{2-[4-[1-(4-fluoro-2-hydroxy-phenyl)-methanoyl]-piperidine-1-yl]-ethylamino}-2-methyl-2H-pyridazine-3-one, 5-{2-[4-[1-(4-fluoro-2-hydroxy-phenyl)-methanoyl]-piperidine-1-yl]-ethylamino}-2H-pyridazine-3-one, 5-{2-[4-[1-(4-fluoro-2-hydroxy-phenyl)-methanoyl]-piperidine-1-yl]-propylamino}-2-methyl-2H-pyridazine-3-one and a pharmaceutically acceptable acid addition salt thereof as active ingredient.

According to a further aspect of the present invention there is provided the use of a piperidinyl-alkylamino-pyridazinone derivative of the general Formula I (wherein X, Y, R, n and Hal are as stated above or a pharmaceutically acceptable acid addition salt thereof for the manufacture of anxiolytic pharmaceutical compositions.

According to a still flirter aspect of the present invention there is provided a method of treatment of human anxiety disorders which comprises administering to a patient in need of such treatment a therapeutically efficient amount of piperidinyl-alkylamino-pyridazinone derivatives of the general Formula I (wherein X, Y, R, n and Hal are as stated above or a pharmaceutically acceptable acid addition salt thereof.

Further details of the present invention are to be found in the following Examples without limiting the scope of protection to said Examples.

EXAMPLES

I.

Starting Materials

A) 5-{2-[4-(6-fluoro-1,2-benzisoxazole-3-yl)-piperidine-1-yl]-ethylamino}-4-chloro-2-methyl-2H-pyridazine-3-one 1.9 g (8.6 millimoles) of 4-chloro-5-(2-choroethylamino)-2-methyl-2H-pyridazine-3-one, 40 ml of acetonitrile, 2.07 g (9.4 millimoles) of 6-fluoro-3-piperidine-4-yl-1,2-benzisoxazole, 2.36 g of potassium carbonate and 0.17 g potassium iodide are admixed. The reaction mixture is heated to boiling for 24 hours, filtered over a magnesium sulfate containing carbon bed and the organic phase is evaporated. The crude product is dissolved in ethyl acetate, washed with water, the organic phase is dried over magnesium sulfate, filtered and evaporated. The crude product is recrystallized from ethyl acetate. Thus 2.8 g of the desired compound are obtained, yield 80.5%. Mp.: 145–147° C.

Elementary analysis: for the Formula $C_{19}H_{21}ClFN_5O_2$ (405.86)

| | | | | |
|---|---|---|---|---|
| calc.: | C 56.23% | H 5.22% | N 17.26% | Cl 8.74% |
| found: | C 55.73% | H 5.26% | N 16.98% | Cl 8.98% |

IR (KBr): 3278, 1635, 1616.

$^1$H-NMR (CDCl$_3$, i400): 7.66 (dd, J1=5.1 Hz, J2=8.7 Hz, 1H), 7.56 (s, 1H), 7.25 (dd, J1=2.1 Hz, J2=8.5 Hz, 1H), 7.07 (~td, Jd=2.1 Hz, Jt=8.8 Hz, 1H), 5.62 (bt, 1H), 3.76 (s, 3H), 3.40 (~q, J=5.6 Hz, 2H), 3.13 (m, 1H), 3.04 (m, 2H), 2.75 (t, J=6.0 Hz, 2H), 2.32 (m, 2H), 2.10 (m, 4H).

$^{13}$C-NMR (CDCl$_3$, i400): 164.03 (d, J=250.6 Hz), 163.81 (d, J=13.4 Hz), 160.71, 157.75, 144.04, 125.62, 122.35 (d, J=11.1 Hz), 117.13, 112.39 (d, J=25.6 Hz), 107.40, 97.40 (d, J=27.1 Hz), 56.02, 52.92, 40.11, 39.23, 34.20, 30.48.

B) 5-{2-[4-(6-fluoro-1,2-benzisoxazole-3-yl)-piperidine-1-yl]-ethylamino}-4-chloro-2H-pyridazine-3-one 5.6 g (22.2 millimoles) of 5-(2-bromoethylamino)-4-chloro-2H-pyridazine-3-one, 16 ml of anhydrous dimethyl formamide, 5.62 g (25.5 millimoles) of 6-fluoro-3-piperidine-4-yl-1,2-benzisoxazole, 8.85 ml of triethyl amine and 0.44 g of potassium iodide are admixed. The reaction mixture is heated at 60° C. for 2 hours, cooled to room temperature and a solution of 5.46 g of sodium carbonate and 50 ml of water is added dropwise. The mixture is stirred for half an hour, the suspension is filtered and the filtered product is washed three times with 20 ml of water each. The crude product thus obtained is dissolved in a 9:1 mixture of acetonitrile and water under heating to boiling, filtered warm and the mother lye is evaporated to one-third of its volume. The residual mother lye is stirred under cooling with icecold water for 2 hours. The precipitated crystals are filtered. Thus 6.75 g of the desired compound are obtained. Yield 77.6%. Mp.: 229–231° C.

Elementary analysis: for the Formula $C_{18}H_{19}ClFN_5O_2$ (391,84)

| calc.:  | C 55.18% | H 4.89% | Cl 9.05% | N 17.87% |
| --- | --- | --- | --- | --- |
| found: | C 54.79% | H 4.94% | Cl 8.75% | N 17.56% |

IR (KBr): 3305, 3141, 1641, 1607.

$^1$H-NMR (DMSO-$d_6$, i400): 12.58 (bs, 1H), 7.96 (dd, J1=5.3 Hz, J2=8.8 Hz, 1H), 7.88 (s, 1H), 7.68 (dd, J1=2.1 Hz, J2=9.1 hz, 1H), 7.30 (~td, Jd=2.1 Hz, Jt=9.1 Hz, 1H), 6.42 (bt, J=5.9 Hz, 1H), 3.47 (~q, J=6.1 Hz, 2H), 3.15 (m, 1H), 3.01 (m, 2H), 2.57 (t, J=6.2 Hz, 2H), 2.23 (m, 2H), 2.02 (m, 2H), 1.80 (m, 2H).

$^{13}$C-NMR (DMSO-$d_6$, i400): 163.79 (d, J=248.0 Hz), 163.18 (d, J=14.1 Hz), 161.46, 157.98, 145.28, 128.09, 127.96, 123.90 (d, J=11.0 Hz), 123.80 (d, J=8.7 Hz), 117.37 (d, J=0.8 Hz), 112.72 (d, J=24.0 Hz), 112.66 (d, J=24.8 Hz), 104.40, 97.61 (d, J=27.1 Hz), 97.45 (d, J=27.5 Hz), 57.23, 57.40, 53.12, 39.70, 33.54, 33.44, 30.40.

C) 4-chloro-5-{3-[4-(6-fluoro-1,2-benzisoxazole-3-yl)-piperidine-1-yl]-propylamino}-2-methyl-2H-pyridazine-3-one 2.4 g (10 millimoles) of 4-chloro-5-(2-chloropropylamino)-2-methyl-2H-pyridazine-3-one, 40 ml of acetonitrile, 2.46 g (11 millimoles) of 6-fluoro-3-piperidine-4-yl-1,2-benzisoxazole, 2.8 g of potassium carbonate and 0.18 g potassium iodide are admixed. The reaction mixture is heated to boiling under stirring for 24 hours, cooled to room temperature and filtered. The filtered product is suspended in 100 ml of water under stirring and refiltered. The crude product is recrystallized from acetonitrile. Thus 2.4 g of the desired compound are obtained. Yield 57.3%. Mp.: 200–202° C.

Elementary analysis: for the Formula $C_{20}H_{23}ClFN_5O_2$ (419.89)

| calc.:  | C 57.21%, | H 5.52% | N 16.68% | Cl 8.44% |
| --- | --- | --- | --- | --- |
| found: | C 56.78% | H 5.48% | N 16.38% | Cl 8.44% |

IR (KBr): 3348, 1606.

$^1$H-NMR (DMSO-$d_6$, i400): 8.00 (dd, J1=5.3 Hz, J2=8.7 Hz, 1H), 7.91 (s, 1H), 7.68 (dd, J1=2.1 Hz, J2=9.1 Hz, 1H), 7.28 (~dt, Jd=2.1 Hz, Jt=9.0 Hz, 1H), 6.94 (bt, J=5.7 Hz, 1H), 3.58 (s, 3H), 3.42 (~q, J=6.1 Hz, 2H), 3.16 (m, 1H), 3.00 (m, 2H), 2.43 (t, J=6.3 Hz, 2H), 2.07 (m, 4H), 1.89 (m, 2H), 1.74 (~qn, J=6.4 Hz, 2H).

$^{13}$C-NMR (DMSO-$d_6$, i400): 163.81 (d, J=248.0 Hz), 163.15 (d, J=14.1 Hz), 161.56, 156.92, 144.84, 126.58, 123.89 (d, J=11.1 Hz), 117.44, 112.65 (d, J=25.2 Hz), 104.34, 97.27 (d, J=27.5 Hz), 56.07, 53.18, 41.66, 39.59, 33.52, 30.20, 26.08.

D) 5-{2-[4-(6-fluoro-1,2-benzisoxazole-3-yl)-piperidine-1-yl]-ethylamino}-2-methyl-2H-pyridazine-3-one 3.67 g (16.4 millimoles) of 5-(2-chloroethylamino)-2-methyl-2H-pyridazine-3-one-hydrochloride, 90 ml of acetonitrile, 4.05 g (18.4 millimoles) of 6-fluoro-3-piperidine-4-yl-1,2-benzisoxazole, 6.84 g of potassium carbonate and 0.37 g of potassium iodide are admixed. The reaction mixture is stirred under heating to boiling for 24 hours, cooled to room temperature and filtered. To the product 100 ml of water are added and the aqueous phase is extracted five times with 50.0 ml of dichloro methane each. The united organic phases are washed with water, dried over anhydrous magnesium sulfate, filtered and the organic phase is evaporated in vacuo. The residue is suspended in diethyl ether and filtered. The crude product is recrystallized from acetonitrile. Thus 3.4 g of the desired compound are obtained. Yield 55.9%.

M.p.: 200–202° C.

Elementary analysis: for the Formula $C_{19}H_{22}FN_5O_2$ (371, 42)

| calc.:  | C 61.44% | H 5.97% | N 18.86% |
| --- | --- | --- | --- |
| found: | C 62.00% | H 5.98% | N 18.84% |

IR (KBr): 3261, 1620, 1571, 1114.

$^1$H-NMR (CDCl$_3$, i400): 8.01 (dd, J1=5.4 Hz, J2=8.6 Hz, 1H), 7.68 (dd, J1=2.1 Hz, J2=9.1 hz, 1H), 7.53 (s, 1H), 7.28 (dd, J1=2.1 Hz, J2=8.5 Hz, 1H), 6.80 (bt, J=5.9 Hz, 1H), 5.51 (s, 1H), 3.47 (s, 3H), 3.16 (m, 1H), 3.15 (m, 2H), 3.01 (m, 2H), 2.52 (m, 2H), 2.19 (m, 2H), 2.05 (m, 2H), 1.84 (m, 2H)

$^{13}$C-NMR (DMSO-$d_6$, i400): 163.80 (d, J=247.6 Hz), 163.16 (d, J=14.1 Hz), 161.52, 161.03, 149.17, 131.01, 123.95 (d, J=11.4 Hz), 117.44, 112.65 (d, J=25.2 Hz), 97.50 (d, J=27.5 Hz), 94.40, 56.11, 53.16, 39.49, 38.29, 33.54, 30.22

E) 5-{3-[4-(6-fluoro-1,2-benzisoxazole-3-yl)-piperidine-1-yl]-propylamino}-2-methyl-2H-pyridazine-3-one 4.12 g (17.3 millimoles) of 5-(3-chloropropylamino)-2-methyl-2H-pyridazine-3-one-hydrochloride, 100 ml of acetonitrile, 4.29 g (19.5 millimoles) of 6-fluoro-3-piperidine-4-yl-1,2-benzisoxazole, 7.24 g of potassium carbonate and 0.39 g of potassium iodide are admixed. The reaction mixture is heated to boiling under stirring for 24 hours, cooled to room temperature and filtered. To the product 100 ml of water are added and the aqueous phase is extracted five times with 90 ml of dichloro methane each. The united organic phases are washed with a saturated sodium chloride solution; dried over magnesium sulfate and filtered over activated charcoal. The organic filtrate is evaporated in vacuo. The residue is suspended in diethyl ether and filtered. The crude product is recrystallized from acetonitrile. Thus 4.14 g of the desired compound are obtained. Yield 62.2%. M.p.: 163–165° C.

Elementary analysis: for the Formula $C_{20}H_{24}FN_5O_2$ (385, 44)

| calc.:  | C 62.32% | H 6.28% | N 18.17% |
| --- | --- | --- | --- |
| found: | C 62.18% | H 6.27% | N 18.09% |

IR (KBr): 3264, 1624, 1591, 1119.

$^1$H-NMR (CDCl$_3$, i400): 7.71 (dd, J1=5.0 Hz, J2=8.7 Hz, 1H), 7.32 (s, 1H), 7.26 (dd, J1=2.1 Hz, J2=8.4 Hz, 1H), 7.10 (dt, Jd=2.1 Hz, Jt=8.8 Hz, 1H), 6.48 (b, 1H), 5.65 d, J=2.7 Hz, 1H), 3.66 (s, 3H), 3.22 (m, 5H), 2.72 (m, 2H), 2.42 (m, 2H), 2.42 (m, 4H), 1.93 (m, 2H)

$^{13}$C-NMR (DMSO-$d_6$, i400): 164.26 (d, J=251.8 Hz), 164.00 (d, J=13.7 Hz), 162.23, 160.42, 148.81, 130.69, 122.29 (d, J=11.1 Hz), 117.22, 112.61 (d, J=25.2 Hz), 97.52 (d, J=26.7 Hz), 96.38, 57.21, 53.22, 42.31, 38.94, 33.70, 30.16, 23.92

F) 5-{2-[4-(6-fluoro-1,2-benzisoxazole-3-yl)-piperidine-1-yl]-ethylamino}-2H-pyridazine-3-one 2.72 g (12.9 millimoles) of 5-(2-chloroethylamino)-2H-pyridazine-3-one-hydrochloride, 11 ml of anhydrous dimethyl formamide, 5.0 g (22.7 millimoles) of 6-fluoro-3-piperidine-4-yl-1,2-benzisoxazole, 6.3 ml of triethyl amine and 0.21 g of potassium iodide are admixed. The reaction mixture is heated to boiling under stirring for 8 hours, cooled to room temperature and filtered. To the mother lye a solution of 2.6 g of sodium hydrogen carbonate and 40 ml of water is added dropwise. The precipitate is filtered, suspended in 100 ml of dichloro methane, stirred for 30 minutes and filtered. The crude product is recrystallized from a 4:1 mixture of water and acetonitrile. The crystals are filtered off. Thus 2.98 g of the desired compound are obtained. Yield 64.6%. M.p.: 97–99° C.

Elementary analysis: for the Formula $C_{18}H_{20}FN_5O_2$ (357, 39)

| calc.: | C 60.49% | H 5.64% | N 19.60% |
|---|---|---|---|
| found: | C 59.97% | H 5.74% | N 19.28% |

IR (KBr): 3261, 1616, 1272, 1176

$^1$H-NMR (DMSO-$d_6$, i400): 11.92 (bs, 1H), 8.00 (dd, J1=5.0 Hz, J2=8.8 Hz, 1H), 7.68 (dd, J1=2.2 Hz, J2=9.2 hz, 1H), 7.52 (d, J=2.6 Hz, 1H), 7.28 (td, Jd=2.2 Hz, Jt=9.0 Hz, 1H), 6.84 (bt, J=5.2 Hz, 1H), 5.42 (d, J=2.4 Hz, 1H), 3.15 (m, 1H), 3.01 (m, 2H), 3.02 (m, 2H), 2.56 (t, J=6.5 Hz, 2H), 2.20 (m, 2H), 2.03 (m, 2H), 1.87 (m, 2H).

$^{13}$C-NMR (DMSO-$d_6$, i400): 163.80 (d, J=248.0 Hz), 163.16 (d, J=14.1 Hz), 162.34, 161.5, 149.43, 131.67, 123.93 (d, J=11.4 Hz), 117.42, 112.64 (d, J=25.2 Hz), 97.49 (d, J=27.1 Hz), 94.36, 56.10, 57.40, 53.16, 39.37, 33.56, 30.22

II.

End Products

Example 1

5-{2-[4-[1-(4-fluoro-2-hydroxy-phenyl)-methanoyl]-piperidine-1-yl]-ethylamino}-2-methyl-2H-pyridazine-3-one Into a pressure-tight hydrogenating apparatus 5.0 g (0.0123 mole) of 5-{2-[4-(6-fluoro-1,2-benzisoxazole-3-yl)-piperidine-1-yl]-ethylamino}-4-chloro-2-methyl-2H-pyridazine-3-one, 450 ml of a solvent mixture (a 9:1 mixture of methanol and distilled water), 0.56 g (0.014 mole) of sodium hydroxide and 10 g of a palladium/charcoal catalyst (composition: 8% of palladium, 28% of carbon, 64% of water) are weighed in. The reaction mixture is stirred at room temperature under a hydrogen pressure of 10 atm. for 16 hours. The unreacted hydrogen is removed from the apparatus, the reaction mixture is heated to reflux temperature and stirred at this temperature for 5 minutes. The mixture is filtered hot and the palladium charcoal catalyst is washed three times with 33 ml of a 1:1 mixture of methanol and dichloro methane each. The united mother lyes are evaporated to 15 ml and stirred under cooling with icecold water for half an hour. The precipitated crystals are filtered off. The crude product is recrystallized from 2-propanol. Thus 3.12 g of the desired compound are obtained. Yield 67.8%.

M.p.: 200–202° C.

Elementary analysis: for the Formula $C_{19}H_{23}FN_4O_3$ (374, 42)

| calc.: | C 60.55% | H 6.19% | N 14.96% |
|---|---|---|---|
| found: | C 60.89% | H 5.89% | N 14.82% |

IR (KBr): 3272, 1621, 1264, 986.

$^1$H-NMR (DMSO-$d_6$, i400): 8.02 (dd, J=6.8 Hz, J2=8.4 Hz, 1H), 7.53 (d, J=2.7 Hz, 1H), 6.8 (m, 3H), 5.49 (d, J=2.6 Hz, 1H), 3.47 (s, 3H), 3.44 (m), 3.11 (~q, J=6.0 Hz, 2H), 2.95 (m, 2H), 2.51 (t, J=6.4 Hz, 2H), 2.12 (m, 2H), 1.78 (m, 2H), 1.64 (m, 2H).

$^{13}$C-NMR (CDCl$_3$, i400): 207.53, 166.36 (d, J=253.4 Hz), 163.48 (d, J=14.1 Hz), 161.04, 149.15, 133.65 (d, J=11.4 Hz), 131.01, 117.13 (d, J=2.3 Hz), 107.15 (d, J=22.5 Hz), 104.47 (d, J=23.7 Hz), 94.36, 56.05, 52.76, 43.82, 39.45, 38.29, 28.51.

Example 2

5-{2-[4-[1-(4-fluoro-2-hydroxy-phenyl)-methanoyl]-piperidine-1-yl]-ethylamino}-2H-piridazine-3-one-dihydrochloride Into a pressure-tight hydrogenating apparatus 3.5 g (0.009 mole) of 5-{2-[4-(6-fluoro-1,2-benzisoxazole-3-yl)-piperidine-1-yl]-ethylamino}-4-chloro-2H-pyridazine-3-one, 350 ml of a solvent mixture (1:1 mixture of methanol and dichloro methane), 0.4 g (0.01 mole) of sodium hydroxide and 7 g of a palladium charcoal catalyst (composition: 8% of palladium, 28% of carbon, 64% of water) are weighed in. The reaction mixture is stirred at a hydrogen pressure of 10 atm. for 16 hours. Hydrogen is removed from the apparatus. The reaction mixture is heated to reflux temperature and stirred at this temperature for 5 minutes. The mixture is filtered hot and the catalyst is washed five times with 350 ml of a 1:1 mixture of methanol and dichloro methane each. The united mother-lyes are evaporated in vacuo. The crude product is dissolved in a 9:1 mixture of 2-propanol and water under stirring and reflux, filtered and the filtrate is evaporated to 100 ml. The mixture is stirred under cooling with icecold water for half an hour. The precipitated crystals are filtered, suspended in a 9:1 mixture of 2-propanol and water and the suspension is acidified by adding concentrated aqueous hydrochloric acid. To the suspension under reflux a 9:1 mixture of 2-propanol and water is added until a clear solution is obtained. The solution is filtered warm, the filtrate is evaporated to 15 ml, the concentrate is stirred under cooling with icecold water and the crystals are filtered off. Thus 1.95 g of the desired compound are obtained. Yield 50.4%. M.p.: 267–269° C.

Elementary analysis: for the Formula $C_{18}H_{23}Cl_2FN_4O_3$ (433,31)

| calc.: | C 49.89% | H 5.35%. | Cl 16.36%, | N 12.93% |
|---|---|---|---|---|
| found: | C 49.29% | H 5.37% | Cl 16.61%, | N 12.60% |

IR (KBr): 3417, 3249, 3070, 1633.

$^1$H-NMR (DMSO-$d_6$, i400): 13.04 (b, 1H), 12.10 (b, 1H), 11.04 (b, 1H), 8.32 (b, 1H), 7.96 (dd, $J_1$=7.0 Hz, $J_2$=8.9 Hz, 1H), 7.84 (~s, 1H), 6.94 (dd, $J_1$=2.6 Hz, $J_2$=10.9 Hz, 1H), 6.82 (~td, $J_d$=2.6 Hz, $J_t$=8.6 Hz, 1H), 6.05 (b), 5.96 (~s, 1H), 3.73 (m, 1H), 3.64 (m, 4H), 3.16 (m, 2H), 2.03 (m, 4H).

Example 3

5-{2-[4-[1-(4-fluoro-2-hydroxy-phenyl)-methanoyl]-piperidine-1-yl]-propylamino}-2-methyl-2H-pyridazine-3-one Into a pressure-tight hydrogenating apparatus 1.64 g (0.0039 mole) of 5-{2-[4-(6-fluoro-1,2-benzisoxazole-3-yl)-piperidine-1-yl]-propylamino}-4-chloro2-methyl-2H-pyridazine-3-one, 150 ml of a solvent mixture (9:1 mixture of methanol and distilled water), 0.18 g (0.0456 mole) of sodium hydroxide and 3.2 g of a palladium/charcoal catalyst (composition: 8% of palladium, 28% of carbon and 64% of water) are weighed in. The reaction mixture is stirred at a hydrogen pressure of 10 atm. for 24 hours. The reaction mixture is heated to reflux temperature and stirred at this temperature for 5 minutes. The mixture is filtered hot and the catalyst is washed five times with 33 ml of a 1:1 mixture of methanol and dichloro methane each. The united mother lyes are evaporated. The precipitated crude product is recrystallized from a mixture of acetonitrile and water. Thus 1.12 g of the desired compound are obtained. Yield 73.8%.

M.p.: 199–201° C.

Elementary analysis: for the Formula $C_{20}H_{25}FN_4O_3$ (388, 45)

| | | | |
|---|---|---|---|
| calc.: | C 61.84% | H 6.49% | N 14.42% |
| found: | C 61.29% | H 6.14% | N 14.28% |

IR (KBr): 3290, 1620, 1599, 1120.

$^1$H-NMR (DMSO-$d_6$, i400): 8.01 (m, 1H), 7.42 (d, J=2.7 Hz, 1H), 6.92 (bt; J=5.3 Hz, 1H), 6.79 (m, 2H), 5.46 (d, J=2.7 Hz, 1H), 3.46 (s, 3H), 3.40 (m, 1H), 3.02 (~q, J=6.3 Hz, 2H), 2.89 (m, 2H), 2.35 (t, J=6.8 Hz, 2H), 2.03 (m, 2H), 1.77 (m, 2H), 1.67 (~qn, J=6.8 Hz, 2H), 1.60 (m, 2H).

What we claim is:

1. Piperidinyl-alkylamino-pyridazinone derivatives of the Formula (I)

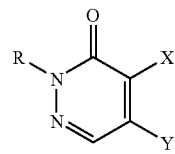

(I)

wherein

R is hydrogen or $C_{1-4}$-alkyl;

one of X and Y stands for hydrogen and the other represents a group of the Formula (II)

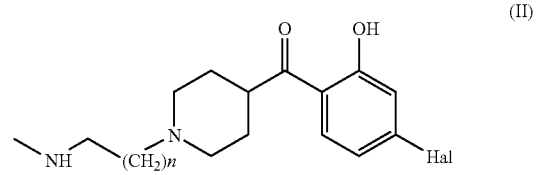

(II)

Hal stands for halogen; and n is 1 or 2, and pharmaceutically acceptable acid addition salts thereof.

2. Piperidinyl-alkylamino-pyridazinone derivatives of the Formula I according to claim 1, wherein Y stands for a group of the Formula II;

X represents hydrogen; and

R, Hal and n are as stated in claim 1, and pharmaceutically acceptable acid addition salts thereof.

3. Piperidinyl-alkylamino-pyridazinone derivatives of the Formula I wherein

Y stands for a group of the Formula II;

X represents hydrogen;

R stands for methyl;

Hal stands for fluorine; and n is 1 or 2, and pharmaceutically acceptable acid addition salts thereof.

4. The following compounds of the Formula I according to claim 1:

5-{2-[4-[1-(4-fluoro-2-hydroxy-phenyl)-methanoyl]-piperidine-1-yl]-ethylamino}-2-methyl-2H-pyridazine-3-one, 5-{2-[4-[1-(4-fluoro-2-hydroxy-phenyl)-methanoyl]-piperidine-1-yl]-ethylamino}-2H-pyridazine-3-one, 5-{2-[4-[1-(4-fluoro-2-hydroxy-phenyl)-methanoyl]-piperidine-1-yl]-propylamino}-2-methyl-2H-pyridazine-3-one, and pharmaceutically acceptable acid addition salts thereof.

5. Process for the preparation of piperidinyl-alkylamino-pyridazinone derivatives of the Formula I of claim 1, wherein Y, X, R, n and Hal are as stated in claim 1, and pharmaceutically acceptable acid addition salts thereof; which comprises a) for the preparation of compounds of the Formula I, wherein Y stands for a group of the Formula II and X, R, n and Hal are as stated in claim 1, subjecting a benzisoxazolyl-piperidinyl-alkylamino-pyridazinone derivative of the Formula I wherein Y stands for a group of the Formula (III)

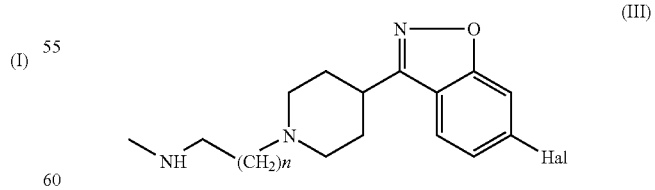

(III)

X stands for hydrogen or chlorine and R, Hal and n are as stated in claim 1 to catalytic hydrogenation; or b) for the preparation of compounds of the Formula I, wherein X stands for a group of the Formula II and Y, R, Hal and n are as stated in claim 1, subjecting a benzisoxazolyl-piperidinyl-alkylamino-pyridazinone derivative of the Formula I, wherein X is a group of the Formula III, Y stands for hydrogen or chlorine and R, Hal and n are as stated in claim 1, to catalytic hydrogenation;

and if desired converting a piperidinyl-alkylamino-pyridazinone derivative of the Formula I thus obtained into a pharmaceutically acceptable acid addition salt thereof or setting free the base from its acid addition salt.

6. Pharmaceutical composition comprising as active ingredient a piperidinyl-alkylamino-pyridazinone derivative of the Formula I of claim 1, wherein X, Y, R, Hal and n are as stated in claim 1, or a pharmaceutically acceptable acid addition salt thereof in admixture with usual carrier(s).

7. Pharmaceutical composition according to claim 6 comprising as active ingredient piperidinyl-alkylamino-pyridazinone derivatives of the Formula I in which X represents hydrogen; R represents hydrogen or $C_{1-4}$-alkyl; Hal stands for halogen; and n is 1 or 2, or a pharmaceutically acceptable acid addition salt thereof.

8. Pharmaceutical composition as stated in claim 7 comprising as active ingredient piperidinyl-alkylamino-pyridazinone derivatives of the Formula I in which X represents hydrogen; R represents methyl; Hal stands for flourine; and n is 1 or 2, or a pharmaceutically acceptable acid addition salt thereof.

9. Pharmaceutical composition according to claim 6 comprising as active ingredient a following compound:

5-{2-[4-[1-(4-fluoro-2-hydroxy-phenyl)-methanoyl]-piperidine-1-yl]-ethylamino}-2-methyl-2-pyridazine-3-one, 5-{2-[4-[1-(4-fluoro-2-hydroxy-phenyl)-methanoyl]-piperidine-1-yl]-ethylamino}-2H-pyridazine-3-one, 5-{2-[4-[1-(4-fluoro-2-hydroxy-phenyl)-methanoyl]-piperidine-1-yl]-propylamino}-2-2H-pyridazine-3-one, and pharmaceutically acceptable acid addition salts thereof.

10. A process for the preparation of a pharmaceutical composition, comprising:

admixing a therapeutically effective amount of a compound of Formula I of claim 1, wherein X, Y, R, n and Hal are as stated in claim 1, or a pharmaceutically acceptable acid addition salt thereof as an active ingredient with suitable pharmaceutical carriers and/or auxiliary agents; and forming the admixture into a pharmaceutically acceptable dosage form.

* * * * *